US011701347B2

(12) United States Patent
Scholz

(10) Patent No.: US 11,701,347 B2
(45) Date of Patent: Jul. 18, 2023

(54) USE OF 5-FLUORO-4-(4-FLUORO-2-METHOXYPHENYL)-N-{4-[(S-METHYLSULFONIMIDOYL)METHYL]PYRIDIN-2-YL}PYRIDIN-2-AMINE FOR TREATING DIFFUSE LARGE B-CELL LYMPHOMA

(71) Applicants: Bayer Aktiengesellschaft, Leverkusen (DE); Bayer Pharma Aktiengesellschaft, Berlin (DE)

(72) Inventor: Arne Scholz, Berlin (DE)

(73) Assignees: BAYER AKTIENGESELLSCHAFT, Leverkusen (DE); BAYER PHARMA AKTIENGESELLSCHAFT, Berlin (DE)

(*) Notice: Subject to any disclaimer, the term of this patent is extended or adjusted under 35 U.S.C. 154(b) by 143 days.

(21) Appl. No.: 16/969,460

(22) PCT Filed: Feb. 12, 2019

(86) PCT No.: PCT/EP2019/053407
§ 371 (c)(1),
(2) Date: Aug. 12, 2020

(87) PCT Pub. No.: WO2019/158517
PCT Pub. Date: Aug. 22, 2019

(65) Prior Publication Data
US 2021/0015806 A1 Jan. 21, 2021

(30) Foreign Application Priority Data
Feb. 13, 2018 (EP) ..................................... 18156576

(51) Int. Cl.
A61K 31/444 (2006.01)
A61P 35/00 (2006.01)
A61K 31/53 (2006.01)
(52) U.S. Cl.
CPC ............ *A61K 31/444* (2013.01); *A61K 31/53* (2013.01); *A61P 35/00* (2018.01)
(58) Field of Classification Search
CPC .................................................. A61K 31/444
See application file for complete search history.

(56) References Cited

U.S. PATENT DOCUMENTS

| 7,291,616 | B2 | 11/2007 | Bhatt et al. |
| 7,618,968 | B2 | 11/2009 | Bhatt et al. |
| 9,242,937 | B2 | 1/2016 | Ruhter et al. |
| 9,650,340 | B2 | 5/2017 | Lucking et al. |
| 9,877,954 | B2 | 1/2018 | Lucking et al. |
| 2003/0153570 | A1 | 8/2003 | Bhatt et al. |
| 2004/0116388 | A1 | 6/2004 | Armistead et al. |
| 2004/0209895 | A1 | 10/2004 | Luecking et al. |
| 2005/0176743 | A1 | 8/2005 | Luecking et al. |
| 2007/0191393 | A1 | 8/2007 | Lucking et al. |
| 2007/0232632 | A1 | 10/2007 | Lucking et al. |
| 2008/0064700 | A1 | 3/2008 | Bhatt et al. |
| 2010/0184789 | A1 | 7/2010 | Wabnitz et al. |
| 2011/0028492 | A1 | 2/2011 | Barsanti et al. |
| 2011/0306602 | A1 | 12/2011 | Wabnitz et al. |

FOREIGN PATENT DOCUMENTS

| CN | 107427520 A | 12/2017 |
| DE | 2129678 A1 | 12/1971 |
| EP | 1218360 B1 | 5/2008 |
| EP | 2527332 A1 | 11/2012 |
| WO | WO-0125220 A1 | 4/2001 |
| WO | WO-02059110 A1 | 8/2002 |
| WO | WO-02066481 A1 | 8/2002 |
| WO | WO-03037346 A1 | 5/2003 |
| WO | WO-2004009562 A1 | 1/2004 |
| WO | WO-2004072063 A1 | 8/2004 |
| WO | WO-2005026129 A1 | 3/2005 |
| WO | WO-2005037800 A1 | 4/2005 |
| WO | WO-2006037945 A1 | 4/2006 |
| WO | WO-2006064251 A1 | 6/2006 |
| WO | WO-2007071455 A1 | 6/2007 |
| WO | WO-2008025556 A1 | 3/2008 |
| WO | WO-2008028590 A1 | 3/2008 |
| WO | WO-2008060248 A1 | 5/2008 |
| WO | WO-2008079918 A1 | 7/2008 |
| WO | WO-2008079933 A2 | 7/2008 |
| WO | WO-2008109943 A1 | 9/2008 |
| WO | WO-2008129070 A1 | 10/2008 |

(Continued)

OTHER PUBLICATIONS

Rowland, Taylor, et al. "Selective Targeting Cyclin-Dependent Kinase-9 (CDK9) Downmodulates c-MYC and Induces Apoptosis in Diffuse Large B-Cell Lymphoma (DLBCL) Cells." Blood. (2016), vol. 128, Issue 22, pp. 289-291. (Year: 2016).*
International Search Report dated Apr. 10, 2019 for International Application No. PCT/EP2019/053407, filed Feb. 12, 2019, 4 pages.
Rowland, T. et al. (Dec. 2, 2016) Selective Targeting Cyclin-Dependent Kinase-9 (CDK9) Downmodulates c-MYC and Induces Apoptosis in Diffuse Large B- Cell Lymphoma (DLBCL) Cells, blood, retrieved from http://www.bloodjournal.org/content/128/22/289 on Mar. 21, 2019, 7 pages.

(Continued)

*Primary Examiner* — John S Kenyon
(74) *Attorney, Agent, or Firm* — Wilson Sonsini Goodrich & Rosati

(57) ABSTRACT

The present invention relates to the use of 5-Fluoro-4-(4-fluoro-2-methoxyphenyl)-N-{4-[(S-methylsulfonimidoyl)methyl]pyridin-2-yl}pyridin-2-amine (compound A), more particularly (+)5-Fluoro-4-(4-fluoro-2-methoxyphenyl)-N-{4-[(S-methylsulfonimidoyl)methyl]pyridin-2-yl}pyridin-2-amine (compound A'), for treating diffuse large B-cell lymphoma (DLBCL), especially in germinal-centre B-cell type of diffuse large B-cell lymphoma and especially in diffuse large B-cell lymphoma which cells have an amplification or translocation of the MYC gene and/or BCL2 gene and/or an overexpression of MYC and/or BCL2.

9 Claims, No Drawings

(56) References Cited

FOREIGN PATENT DOCUMENTS

| WO | WO-2008129071 A1 | 10/2008 | |
|----|------------------|---------|---|
| WO | WO-2008129080 A1 | 10/2008 | |
| WO | WO-2008132138 A1 | 11/2008 | |
| WO | WO-2009029998 A1 | 3/2009 | |
| WO | WO-2009032861 A1 | 3/2009 | |
| WO | WO-2009118567 A2 | 10/2009 | |
| WO | WO-2010009155 A2 | 1/2010 | |
| WO | WO-2011012661 A1 | 2/2011 | |
| WO | WO-2011026917 A1 | 3/2011 | |
| WO | WO-2011029537 A1 | 3/2011 | |
| WO | WO-2011046970 A1 | 4/2011 | |
| WO | WO-2011116951 A1 | 9/2011 | |
| WO | WO-2012038411 A1 | 3/2012 | |
| WO | WO-2012066065 A1 | 5/2012 | |
| WO | WO-2012066070 A1 | 5/2012 | |
| WO | WO-2012101062 A1 | 8/2012 | |
| WO | WO-2012101063 A1 | 8/2012 | |
| WO | WO-2012101064 A1 | 8/2012 | |
| WO | WO-2012101065 A2 | 8/2012 | |
| WO | WO-2012101066 A1 | 8/2012 | |
| WO | WO-2012117048 A1 | 9/2012 | |
| WO | WO-2012117059 A1 | 9/2012 | |
| WO | WO-2012139499 A1 | 10/2012 | |
| WO | WO-2012142329 A1 | 10/2012 | |
| WO | WO-2012143399 A1 | 10/2012 | |
| WO | WO-2012160034 A1 | 11/2012 | |
| WO | WO-2013037894 A1 | 3/2013 | |
| WO | WO-2013037896 A1 | 3/2013 | |
| WO | WO-2014060376 A1 | 4/2014 | |
| WO | WO2014/076091 A1 | 5/2014 | |
| WO | WO-2014076028 A1 | 5/2014 | |
| WO | WO-2014076091 A1 * | 5/2014 | ........... A61K 31/444 |
| WO | WO-2015001021 A1 | 1/2015 | |
| WO | WO-2015136028 A1 | 9/2015 | |
| WO | WO-2019158517 A1 | 8/2019 | |

OTHER PUBLICATIONS

Bark-Jones et al. EBV EBNA 2 stimulates CDK9-dependent transcription and RNA polymerase II phosphorylation on serine 5. Oncogene 25:1775-1785 (2006).

Boyle et al. Improving Outcomes in Advanced DLBCL: Systemic Approaches and Radiotherapy. Oncology(Williston Park) 28(12):1074-81 (2014).

Camicia. et al. Novel drug targets for personalized precision medicine in relapsed/refractory diffuse large B-cell lymphoma: a comprehensive review. Mol Cancer. 14:207 (2015).

Chambers et al. Dissemination and Growth of Cancer Cells in Metastatic Sites. Nature Reviews 2:663-672 (2002).

Cho et al. CYCLINg through transcription Posttranslational modification of P-TEFb regulate transcription elongation. Cell Cycle 9(9):1697-1705 (May 1, 2010).

Copeland et al. Drug-target residence time and its implications for lead optimization. Nature Reviews Drug Discovery 5:730-739 (2006).

He et al. A La-Related Protein Modulates 7SK snRNP Integrity to Suppress P-TEFb-Dependent Transcriptional Elongation and Tumorigenesis. Molecular Cell 29:588-599 (Mar. 14, 2008).

Hogan et al., Asymmetric Sulfoxidation of an Aryl Ethyl Sulfide: Modification of Kagan Procedure to Provide a Viable Manufacturing Process. Org. Proc. Res. Dev., 6:225-229 (2002).

Martelli et al. Diffuse large B-cell lymphoma. Crit Rev Oncol Hematol. 87(2):146-171 (2013).

Nastoupil et al. Diffuse Large B-Cell Lymphoma: Current Treatment Approaches. Oncology (Williston Park) 26(5):488-95 (2012).

Polla et al. Design and synthesis of potent, orally active, inhibitors of carboxypeptidase U (TAFIa). Bioorganic & Medicinal Chemistry Letters 12:1151-1175 (2004).

Roman et al. Epidemiology of lymphomas. Histopathology 58:4-14 (2011).

Sammond et al. Discovery of a novel and potent series of dianilinopyrimidineurea and urea isostere inhibitors of VEGFR2 tyrosine kinase. Bioorganic & Medicinal Chemistry Letters 15:3519-3523 (2005).

Sehn et al. Gascoyne RD. Diffuse large B-cell lymphoma: optimizing outcome in the context of clinical and biologic heterogeneity. Blood. 125:22-32 (2015).

U.S. Appl. No. 14/443,279 Office Action dated May 20, 2016.

U.S. Appl. No. 15/477,974 Office Action dated May 10, 2017.

Wang et al. Discovery and Characterization of 2-Anilino-4-(Thiazol-5-yl)Pyrimidine Transcriptional CDK Inhibitors as Anticancer Agents. Chemistry & Biology 17:1111-1121 (2010).

Yang et al. Recruitment of P-TEFb for stimulation of transcriptional elongation by the bromodomain protein Brd4. Mol. Cell 19:535-545 (2005).

Zhou et al. Coordination of Transcription Factor Phosphorylation and Histone Methylation by the P-TEFb Kinase during Human Immunodeficiency Virus Type 1 Transcription.Journal of Virology 78(24):13522-13533 (Dec. 2004).

Zhou et al. Tax interacts with P-TEFb in a novel manner to stimulate human T-lymphotropic virus type 1 transcription. J Virol. 80(10):4781-4791 (2006).

Zhou et al. The Yin and Yang of P-TEFb Regulation: Implications for Human Immunodeficiency Virus Gene Expression and Global Control of Cell Growth and Differentiation. Microbiology and Molecular Biology Reviews 70(3):646-659 (Sep. 2006).

* cited by examiner

USE OF 5-FLUORO-4-(4-FLUORO-2-METHOXYPHENYL)-N-{4-[(S-METHYLSULFONIMIDOYL)METHYL]PYRIDIN-2-YL}PYRIDIN-2-AMINE FOR TREATING DIFFUSE LARGE B-CELL LYMPHOMA

CROSS REFERENCE TO RELATED APPLICATIONS

This application is a national stage application under 35 U.S.C. § 371 of International Application No. PCT/EP2019/053407, filed internationally on Feb. 12, 2019 which claims benefit of European Application No. 18156576.3, filed Feb. 13, 2018.

The present invention relates to the use of 5-Fluoro-4-(4-fluoro-2-methoxyphenyl)-N-{4-[(S-methylsulfonimidoyl)methyl]pyridin-2-yl}pyridin-2-amine (compound A), more particularly (+)5-Fluoro-4-(4-fluoro-2-methoxyphenyl)-N-{4-[(S-methylsulfonimidoyl)methyl]pyridin-2-yl}pyridin-2-amine (compound A'), for treating diffuse large B-cell lymphoma (DLBCL), especially in germinal-centre B-cell type of diffuse large B-cell lymphoma and especially in diffuse large B-cell lymphoma which cells have an amplification or translocation of the MYC gene and/or BCL2 gene and/or an overexpression of MYC and/or BCL2.

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNA polymerase II via phosphorylation of the carboxy-terminal domain (CTD). Positive transcription factor b (P-TEFb) is a heterodimer of CDK9 and one of four cyclin partners, cyclin T1, cyclin K, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 2010, 9, 1697). P-TEFb is crucially involved in overcoming promoter-proximal pausing of RNA polymerase II and transition into a productive elongation state by phosphorylation of Ser 2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol. Cell 2008, 29, 588).

The remaining half of P-TEFb exists in an active complex containing the bromodomain protein Brd4 (Yang et al., Mol. Cell 2005, 19, 535). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation (Zhou & Yik, Microbiol. Mol. Biol. Rev. 2006, 70, 646). Furthermore, the activity of P-TEFb is regulated by posttranslational modifications including phosphorylation/de-phosphorylation, ubiquitination, and acetylation (reviewed in Cho et al., Cell Cycle 2010, 9, 1697).

Deregulated CDK9 kinase activity of the P-TEFb heterodimer is associated with a variety of human pathological settings such as hyper-proliferative diseases (e.g. cancer), virally induced infectious diseases or cardiovascular diseases.

Cancer is regarded as a hyper-proliferative disorder mediated by a disbalance of proliferation and cell death (apoptosis). High levels of anti-apoptotic Bcl-2-family proteins are found in various human tumours and account for prolonged survival of tumour cells and therapy resistance. Inhibition of P-TEFb kinase activity was shown to reduce transcriptional activity of RNA polymerase II leading to a decline of short-lived anti-apoptotic proteins, especially Mcl-1 and XIAP, reinstalling the ability of tumour cells to undergo apoptosis. A number of other proteins associated with the transformed tumour phenotype (such as Myc, NF-kB responsive gene transcripts, mitotic kinases) are either short-lived proteins or are encoded by short-lived transcripts which are sensitive to reduced RNA polymerase II activity mediated by P-TEFb inhibition (reviewed in Wang & Fischer, Trends Pharmacol. Sci. 2008, 29, 302).

Many viruses rely on the transcriptional machinery of the host cell for the transcription of their own genome. In case of HIV-1 RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 replication at kinase inhibitor concentrations that are not cytotoxic to the host cells (reviewed in Wang & Fischer, Trends Pharmacol. Sci. 2008, 29, 302). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene 2006, 25, 1775), and the human T-lymphotropic virus type 1 (HTLV-1), where the transcriptional activator Tax recruits P-TEFb (Zhou et al., J. Virol. 2006, 80, 4781).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 2007, 6, 1856).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfils multiple roles in regulation of cell proliferation. Thus, co-inhibition of cell cycle CDK's (e.g. CDK1/cyclin B, CDK2/cyclin A, CDK2/cyclinE, CDK4/cyclinD, CDK6/cyclinD) and of CDK9 is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are therefore required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDKS inhibitors (WO2008129071), respectively, but no specific CDK9 IC50 (WO2008129070) or CDKS IC50 (WO200812971) data is presented.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80). EP1218360 B1 describes triazin derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors. Wang et al. (Chemistry & Biology 2010, 17, 1111-1121) describe 2-anilino-4-(thiazol-5-yl)pyrimidine transcriptional CDK inhibitors, which show anticancer activity in animal models.

WO2004009562 discloses substituted triazine kinase inhibitors. For selected compounds CDK1 and CDK 4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618, 968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumour cells.

WO2008025556 describes carbamoyl sulfoximides having a pyrimidine core, which are useful as kinase inhibitors. No CDK9 data is presented.

WO2002066481 describes pyrimidine derivatives as cyclin dependent kinase inhibitors CDK9 is not mentioned and no CDK9 data is presented.

WO2008109943 concerns phenyl aminopyri(mi)dine compounds and their use as kinase inhibitors, in particular as JAK2 kinase inhibitors. The specific examples focus on compounds having a pyrimidine core.

WO2009032861 describes substituted pyrimidinyl amines as JNK kinase inhibitors. The specific examples focus on compounds having a pyrimidine core.

WO2011046970 concerns amino-pyrimidine compounds as inhibitors of TBKL and/or IKK epsilon. The specific examples focus on compounds having a pyrimidine core.

WO2012160034 describes the compounds of the present invention. It is disclosed the compounds inhibit the cell proliferation of HeLa cells (cervical cancer), HeLa/MaTu/ADR cells (cervical cancer), NCI-H460 cells (non-small cell lung cancer), DU145 cells (hormone-independent human prostate cancer), Caco-2 cells (colorectal cancer) and B16F10 cells (melanoma).

The object of the present invention is to improve the treatment of diffuse large B-cell lymphoma (DLBCL).

Treatment of Diffuse Large B-Cell Lymphoma

Malignant neoplasms of B-lymphocytes and T-lymphocytes can be broadly characterised as Hodgkin and non-Hodgkin lymphomas. Non-Hodgkin lymphomas, in turn, represent a large heterogeneous population of diseases each with distinct epidemiology, aetiology, and morphologic, immunophenotypic, and clinical features. The World Health Organisation (WHO) reclassified non-Hodgkin lymphomas in 2008 and this now better reflects our understanding of the disease entities and their relationship to the immune system (Jaffe E S. The 2008 WHO classification of lymphomas: implications for clinical practice and translational research. Hematology Am Soc Hematol Educ Program 2009:523-531).

DLBCL is an aggressive disease and the most common subtype of non-Hodgkin lymphoma accounting for up to 30-40% of newly diagnosed cases in Western countries (Roman E, Smith A G. Epidemiology of lymphomas. Histopathology. 2011;58:4-14). The primary modality for advanced-stage DLBCL is combination chemoimmunotherapy, specifically R-CHOP (rituximab, cyclophosphamide, doxorubicin, vincristine and prednisone). The introduction of rituximab into this chemotherapeutic regime has been the cornerstone to consistent and meaningful improvements in the outcome of DLBCL patients. However, approximately 30 to 40% of patients will develop relapsed or refractory disease that does not respond favourably to, or relapse, following R-CHOP therapy (Camicia R et al. Novel drug targets for personalized precision medicine in relapsed/refractory diffuse large B-cell lymphoma: a comprehensive review. Mol Cancer. 2015;14:207). As a result, a variety of treatment approaches have been explored in an attempt to improve outcomes, including delivery of more chemotherapy cycles, dose-dense and alternative drug combinations and high-dose chemotherapy, followed by autologous stem cell transplant. However, there has been little evidence that these therapies have superior efficacy to R-CHOP.

Gene expression profiling (GEP) studies have identified two distinct molecular subtypes, termed germinal center B cell (GCB)-DLBCL and activated B cell (ABC)-DLBCL, which represent up to 45% and 35%, respectively, of DLBCL-NOS cases (Martelli M, Ferreri A J, Agostinelli C, Di Rocco A, Pfreundschuh M, Pileri S A. Diffuse large B-cell lymphoma. Crit Rev Oncol Hematol. 2013;87:146-71). A variety of studies have correlated the presence of a MYC translocation with a poorer outcome in DLBCL patients treated with R-CHOP, but newer studies have revealed that concurrent double-hit translocation with BCL2 results in a treatment-refractory patient group with low median survival. This type of double-hit translocation is more common in GCB-DLBCL and represent about 5% of all cases, while the dual overexpression of these two proteins is even more common (25% of DLBCL cases), appears more frequently in ABC-DLBCL, and results in a significantly poorer outcome compared to patients who express only one or neither protein (Johnson N A, Slack G W, Savage K J, et al. Concurrent expression of MYC and BCL2 in diffuse large B-cell lymphoma treated with rituximab plus cyclophosphamide, doxorubicin, vincristine, and prednisone. J Clin Oncol. 2012;30:3452-3459).

Therapeutic targeting of the specific molecular pathways involved in the development of DLBCL may ultimately lead to improvement in patient outcomes. Several novel agents undergoing evaluation, both as single agents in the relapsed-disease setting and in combination with R-CHOP include immunomodulatory drugs (IMiDs), protein kinase C inhibitors, histone deacetylase inhibitors, proteasome inhibitors and mTOR (mammalian target of rapamycin) inhibitors, BTK inhibitors, SYK inhibitors, PKCl3 inhibitors, PI3K inhibitors, as well as BCL2 inhibitors (Sehn L H, Gascoyne R D. Diffuse large B-cell lymphoma: optimizing outcome in the context of clinical and biologic heterogeneity. Blood. 2015;125:22-32; Boyle J et al. Improving Outcomes in Advanced DLBCL: Systemic Approaches and Radiotherapy. Oncology (Williston Park) 2014; 28(12): pii: 202929; Nastoupil L J et al. Diffuse Large B-Cell Lymphoma: Current Treatment Approaches. Oncology (Williston Park) 2012; 26(5):488-95).

Therefore, alternative therapies are needed for DLBCL and particularly for relapse or aggressive disease subsets.

It has now been found that the compound 5-Fluoro-4-(4-fluoro-2-methoxyphenyl)-N-{4-[(S-methylsulfonimidoyl)methyl]pyridin-2-yl}pyridin-2-amine (compound A, formula (I)),

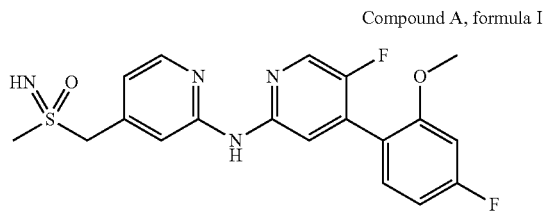 [SMILES: COc1cc(F)ccc1-c1cc(Nc2cc(CS(C)(=N)=O)ccn2)ncc1F]

Compound A, formula I more particularly
(+)-5-Fluoro-4-(4-fluoro-2-methoxyphenyl)-N-{4-[(S-methylsulfonimidoyl)methyl]pyridin-2-yl}pyridin-2-amine (compound A'),
acts in specific tumour types which had previously not yet been contemplated, viz. in diffuse large B-cell lymphoma (DLBCL), especially in germinal-centre B-cell type of diffuse large B-cell lymphoma and especially in diffuse large B-cell lymphoma which cells have an amplification or translocation of the MYC gene and/or BCL2 gene and/or an overexpression of MYC and/or BCL2.

5-Fluoro-4-(4-fluoro-2-methoxyphenyl)-N-{4-[(S-methylsulfonimidoyl)methyl]pyridin-2-yl}pyridin-2-amine (compound A) is a selected sulphoximine-substituted anilinopyrimidine derivative which can be separated into two stereoisomers, viz.:
(+)-5-Fluoro-4-(4-fluoro-2-methoxyphenyl)-N-{4-[(S-methylsulfonimidoyl)methyl]pyridin-2-yl}pyridin-2-amine (compound A') and
(−)-5-Fluoro-4-(4-fluoro-2-methoxyphenyl)-N-{4-[(S-methylsulfonimidoyl)methyl]pyridin-2-yl}pyridin-2-amine (compound A″).

Compound A' is preferred and is in clinical development as Compound A'.

Where compound A is mentioned below, both the pure stereoisomers A' and A″, and also any mixture of these two, are meant thereby.

The present invention is directed to the use of
5-Fluoro-4-(4-fluoro-2-methoxyphenyl)-N-{4-[(S-methylsulfonimidoyl)methyl]pyridin-2-yl}pyridin-2-amine (compound A) or one of its physiologically acceptable salts or enantiomers, more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts,
for the treatment and/or prophylaxis of diffuse large B-cell lymphoma (DLBCL), especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2.

The present application is further directed to the use of
5-Fluoro-4-(4-fluoro-2-methoxyphenyl)-N-{4-[(S-methylsulfonimidoyl)methyl]pyridin-2-yl}pyridin-2-amine (compound A) or one of its physiologically acceptable salts or enantiomers, more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts,
for preparing a medicament for treating diffuse large B-cell lymphoma (DLBCL), especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2.

Another aspect of the present invention is the
use of 5-Fluoro-4-(4-fluoro-2-methoxyphenyl)-N-{4-[(S-methylsulfonimidoyl)methyl]pyridin-2-yl}pyridin-2-amine (compound A) according to formula (I) or one of its physiologically acceptable salts or enantiomers

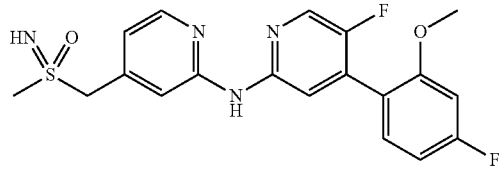 [SMILES: COc1cc(F)ccc1-c1cc(Nc2cc(CS(C)(=N)=O)ccn2)ncc1F]

compound A, formula I more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts
in the manufacture of a medicament for treating cancer in a subject, wherein the medicament is manufactured for treating diffuse large B-cell lymphoma (DLBCL), especially germinal-centre B-cell type of diffuse large B-cell lymphoma and especially diffuse large B-cell lymphoma which cells have an amplification or translocation of the MYC gene and/or BCL2 gene and/or an overexpression of MYC and/or BCL2.

The present application further provides
5-Fluoro-4-(4-fluoro-2-methoxyphenyl)-N-{4-[(S-methylsulfonimidoyl)methyl]pyridin-2-yl}pyridin-2-amine of formula I (compound A) or one of its physiologically acceptable salts or enantiomers compound A, formula I

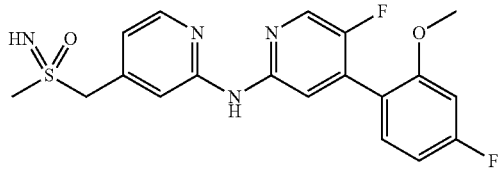

more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts, for the use of treating diffuse large B-cell lymphoma (DLBCL) especially germinal-centre B-cell type of diffuse large B-cell lymphoma and especially diffuse large B-cell lymphoma which cells have an amplification or translocation of the MYC gene and/or BCL2 gene and/or an overexpression of MYC and/or BCL2.

The present invention is also directed to
5-Fluoro-4-(4-fluoro-2-methoxyphenyl)-N-{4-[(S-methylsulfonimidoyl)methyl]pyridin-2-yl}pyridin-2-amine of formula I (compound A) or one of its physiologically acceptable salts or enantiomers compound A, formula I

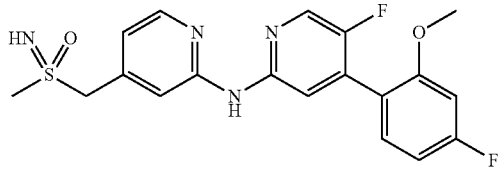

more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts
for the use in a method of treatment and/or prophylaxis of diffuse large B-cell lymphoma (DLBCL) especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2.

Another aspect of the present invention is a method of treatment and/or prophylaxis of diffuse large B-cell lymphoma (DLBCL), especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2, using an effective amount of 5-Fluoro-4-(4-fluoro-2-methoxyphenyl)-N-{4-[(S-methylsulfonimidoyl)methyl]pyridin-2-yl}pyridin-2-amine (compound A) of formula I or one of its physiologically acceptable salts or enantiomers

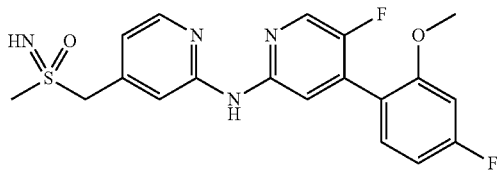

more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts.

The present application further provides pharmaceutical compositions comprising
5-Fluoro-4-(4-fluoro-2-methoxyphenyl)-N-{4-[(S-methylsulfonimidoyl)methyl]pyridin-2-yl}pyridin-2-amine (compound A) or one of its physiologically acceptable salts or enantiomers, more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts, for treating diffuse large B-cell lymphoma (DLBCL), .

The present invention is also directed to pharmaceutical compositions comprising
5-Fluoro-4-(4-fluoro-2-methoxyphenyl)-N-{4-[(S-methylsulfonimidoyl)methyl]pyridin-2-yl}pyridin-2-amine (compound A) of formula I or one of its physiologically acceptable salts or enantiomers compound A, formula I

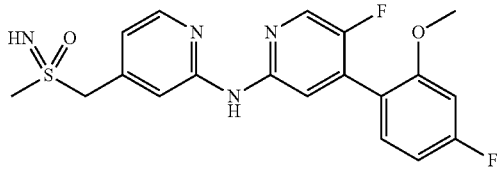

more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts and at least one inert, nontoxic, pharmaceutically suitable adjuvant for the treatment and/or prophylaxis of diffuse large B-cell lymphoma (DLBCL).

The present application further provides combinations of
5-Fluoro-4-(4-fluoro-2-methoxyphenyl)-N-{4-[(S-methylsulfonimidoyl)methyl]pyridin-2-yl}pyridin-2-amine (compound A) or one of its physiologically acceptable salts or enantiomers, more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts, with at least one further active ingredient for treating diffuse large B-cell lymphoma (DLBCL), especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2.

The present invention is also directed to pharmaceutical combinations comprising
5-Fluoro-4-(4-fluoro-2-methoxyphenyl)-N-{4-[(S-methylsulfonimidoyl)methyl]pyridin-2-amine (compound A) of formula I or one of its physiologically acceptable salts or enantiomers

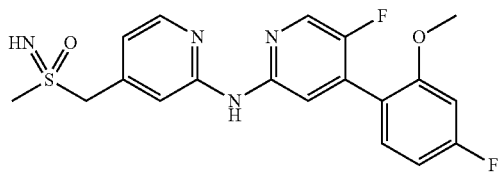 [SMILES: COc1cc(F)ccc1-c1cc(Nc2cc(CS(C)(=N)=O)ccn2)ncc1F]

more particularly
(+)-5-Fluoro-4-(4-fluoro-2-methoxyphenyl)-N-{4-[(S-methylsulfonimidoyl)methyl]pyridin-2-yl}pyridin-2-amine (compound A') or one of its physiologically acceptable salts, and at least one or more further active ingredients for the treatment and/or prophylaxis of diffuse large B-cell lymphoma (DLBCL), especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2.

The use of the physiologically tolerable salts of compound A should likewise be considered to be covered by the present invention.

Physiologically safe salts of compound A encompass acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically safe salts of compound A also encompass salts of customary bases, such as, by way of example and preferably, alkali metal salts (e.g. sodium and potassium salts), alkaline earth metal salts (e.g. calcium and magnesium salts) and ammonium salts derived from ammonia or organic amines having from 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The present invention further provides drugs containing compound A and at least one or more further active ingredients for treating diffuse large B-cell lymphoma (DLBCL), especially of germinal-centre B-cell type of diffuse large B-cell lymphoma and especially of diffuse large B-cell lymphoma which cells have an amplification or translocation of the MYC gene and/or BCL2 gene and/or an overexpression of MYC and/or BCL2.

Compound A may have systemic and/or local activity. For this purpose, it can be administered in a suitable manner, such as, for example, orally, parenterally, via the pulmonary route, nasal, sublingually, lingually, buccally, rectally, vaginally, dermally, transdermally, conjuntivally, otically or as an implant or stent.

For these administration routes, compound A according to the invention may be administered in suitable administration forms.

Suitable for oral administration forms which function according to the prior art and deliver compound A of the invention rapidly and/or in a modified manner and which comprise compound A according to the invention in crystalline and/or amorphised and/or dissolved form, such as, for example, tablets (uncoated or coated tablets, for example with coatings which are resistant to gastric juice or dissolve with a delay or are insoluble and control the release of the compound of the invention), tablets which disintegrate rapidly in the oral cavity, or films/wafers, films/lyophilisates, capsules (for example hard or soft gelatine capsules), sugar-coated tablets, granules, pellets, powders, emulsions, suspensions, aerosols or solutions.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperidoneal). Administration forms which are suitable for parenteral administration are, inter alia, preparations for injection and infusion in the form of solutions, suspensions, emulsions, lyophilisates or sterile powders.

Examples which are suitable for other administration routes are pharmaceutical forms for inhalation [inter alia power inhalers, nebulisers], nasal drops, solutions, sprays; tablets, films/wafers or capsules, to be administered lingually, sublingually or buccaly, suppositories, preparations for the eyes and the ears, eye baths, ocular insert, ear drops, ear powders, ear-rinses, ear tampons, vaginal capsules, aqueous suspensions (lotions, mixturae agitandae), lipophilic suspensions, ointments, creams, transdermal therapeutic systems (such as, for example, patches), milk, pastes, foams, dusting powders, implants or stents.

Compound A can be converted into the stated administration forms. This can be affected in a manner known per se by mixing with inert, non-toxic, pharmaceutically suitable adjuvants. These adjuvants include, inter alia, fillers and excipients (for example cellulose, microcrystalline cellulose, such as, for example, Avicel®, lactose, mannitol, starch, calcium phosphate such as, for example, Di-Cafos®), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat)

solvents (for example water, ethanol, Isopropanol, glycerol, propylene glycol, medium chain-length triglycerides fatty oils, liquid polyethylene glycols, paraffins), surfactants, emulsifiers, dispersants or wetters (for example sodium dodecyle sulphate, lecithin, phospholipids, fatty alcohols such as, for example, Lanette®, sorbitan fatty acid esters such as, for example, Span®, polyoxyethylene sorbitan fatty acid esters such as, for example, Tween®, polyoxyethylene fatty acid glycerides such as, for example, Cremophor®, polyoxethylene fatty acid esters, polyoxyethylene fatty alcohol ethers, glycerol fatty acid esters, poloxamers such as, for example, Pluronic®), buffers and also acids and bases (for example phosphates, carbonates, citric acid, acetic acid, hydrochloric acid, sodium hydroxide solution, ammonium carbonate, trometamol, triethanolamine)

isotonicity agents (for example glucose, sodium chloride),
adsorbents (for example highly-disperse silicas)
viscosity-increasing agents, gel formers, thickeners and/or binders (for example polyvinylpyrrolidon, methylcellulose, hydroxypropylmethylcellulose, hydroxypropylcellulose, carboxymethylcellulose-sodium, starch, carbomers, polyacrylic acids such as, for example, Carbopol®, alginates, gelatine), disintegrants (for example modified starch, carboxymethylcellulose-sodium, sodium starch glycolate such as, for example, Explotab®, cross-linked polyvinylpyrrolidon, croscarmellose-sodium such as, for example, AcDiSol®), flow regulators, lubricants, glidant and mould release agents (for example magnesium stearate, stearic acid, talc, highly-disperse silicas such as, for example, Aerosil®), coating materials (for example sugar, shellac) and film formers for films or diffusion membranes which dissolve rapidly or in a modified manner (for example polyvinylpyrrolidones such as, for example, Kollidon®, polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®), capsule materials (for example gelatine, hydroxypropylmethylcellulose), synthetic polymers (for example polylactides, polyglycolides, polyacrylates, polymethacrylates such as, for example, Eudragit®, polyvinylpyrrolidones such as, for example, Kollidon®, polyvinyl alcohols, polyvinyl acetates, polyethylene oxides, polyethylene glycols and their copolymers and blockcopolymers), plasticisers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to medicaments which comprise at least one compound according to the invention, conventionally together with one or more inert, non-toxic, pharmaceutically suitable adjuvants, and to their use for the above-mentioned purposes.

Dosage and Treatment Regimen

The dosage and the treatment regimen can and must be varied depending on the carcinoma type and the treatment goal.

The daily dose is generally between 20 mg and 850 mg and can be divided into a plurality of identical or different dosage units, preferably 2 which can be taken simultaneously or according to a certain time schedule.

In particular the daily dose is between 30 mg and 500 mg and can be divided into a plurality of identical or different dosage units, preferably 2 which can be taken simultaneously or according to a certain time schedule.

A preferred daily dose is between 20 mg and 400 mg and can be divided into a plurality of identical or different dosage units, preferably 2 which can be taken simultaneously or according to a certain time schedule.

More particularly, the daily dose is between 40 mg and 300 mg and can be divided into a plurality of identical or different dosage units, preferably 2 which can be taken simultaneously or according to a certain time schedule.

A more preferred daily dose is between 20 mg and 200 mg and can be divided into a plurality of identical or different dosage units, preferably 2 which can be taken simultaneously or according to a certain time schedule.

An even more preferred daily dose is between 50 mg and 180 mg and can be divided into a plurality of identical or different dosage units, preferably 2 which can be taken simultaneously or according to a certain time schedule.

This applies both to monotherapy and to combination therapy with other anti-hyperproliferative, cytostatic or cytotoxic substances, the combination therapy possibly requiring a reduction in dose.

The treatment can be carried out in regularly repeated cycles. Treatment cycles may have varying duration, such as 21 days or 28 days, whereby dosing is given continuously, or intermittently. Preferred is a cycle length of 28 days, whereby dosing is given continuously, or intermittently.

Continuous schedules involve daily dosing, for example, 21 daily doses in a 21-day cycle, or 28 daily doses in a 28-day cycle. A preferred continuous schedule is 28 daily doses in a 28-day cycle.

Intermittent schedules involve a period of treatment followed by a period of non-treatment, for example in a cycle of 21 days, or a cycle of 28 days. A preferred cycle duration for an intermittent schedule is 28 days.

The period of treatment may be repeated more than once in a given treatment cycle.

The period of treatment may be for example 1 to 21 days, more preferably 3 to 14 days.

An even more preferred intermittent schedule involves treatment for 3 days followed by non-treatment for 4 days, repeated every week in such a way that a 28-day treatment cycle is completed.

Treatment is successful when there is at least disease stabilisation and the adverse effects occur to an extent which is easily treatable, but at least easily acceptable. Thus, the number of cycles of treatment applied may vary from patient to patient, according to treatment response and tolerability.

Treatment is successful when there is at least disease stabilisation and the adverse effects occur to an extent which is easily treatable, but at least easily acceptable.

Compound A can be used on its own or, if required, in combination with one or more other pharmacologically effective substances, provided said combination does not lead to undesired and unacceptable adverse effects. The present invention therefore further provides drugs containing compound A according to the invention and one or more further active ingredients, in particular for treating and/or preventing the above-mentioned diseases.

For example, compound A can be combined with known anti-hyperproliferative, cytostatic or cytotoxic substances for treating cancers. The combination of the compound A according to the invention with other substances in use for cancer therapy or else with radiotherapy is especially advisable.

Examples of suitable active ingredients for combination purposes include: abraxane, afinitor, aldesleukin, alendronic acid, alfaferone, alitretinoin, allopurinol, aloprim, aloxi, altretamine, aminoglutethimide, amifostine, amrubicin, amsacrine, anastrozole, anzemet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulphate, broxuridine, bortezomib, busulfan, calcitonin, campath, capecitabine, carboplatin, casodex, cefesone, celmoleukin, cerubidine, chlorambucil, cisplatin, cladribine, clodronic acid, cyclophosphamide, cytarabine, dacarbazine, dactinomycin, daunoxome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine sodium phosphate, ethinyl estradiol, ethyol, etidronic acid, etopophos, etoposide, fadrozole, fareston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec,gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon alpha, interferon alpha 2, interferon alpha 2α, interferon alpha 2β, interferon alpha n1, interferon alpha n3, interferon beta, interferon gamma 1a, interleukin 2, intron A, iressa, irinotecan, kytril, lapatinib, lentinan sulphate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, orapred, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, RDEA119, rebif, rhenium-186 etidronate, rituximab, roferon-A, romurtide, salagen, sandostatin, sargramostim, semustine, sizofiran, sobuzoxane, solu-medrol, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran; ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifen, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurin, tipifarnib, tirapazamine, TLK-286, toremifene, transMID-107R, valspodar, vapreotide, vatalanib, verteporfin, vinflunine, Z-100, zoledronic acid, and also combinations thereof.

In a preferred embodiment, compound A of the present invention can be combined with the following active ingredients:

131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alpha, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, methyl amino levulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy-PEG-epoetin beta), pegfilgrastim, peginterferon alfa 2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin, ibrunitib, fostamatinib disodium, enzastaurin, idelalisib, ABT-199, obinutuzumab, carfilzomib, brentuximab vedotin, panobinostat and also combinations thereof Promisingly, compound A can also be combined with biological therapeutics such as antibodies (e.g. avastin, rituxan, erbitux, herceptin, cetuximab) and recombinant proteins.

Compound A can also achieve positive effects in combination with other therapies directed against angiogenesis, such as, for example, with avastin, axitinib, regorafenib, recentin, sorafenib or sunitinib. Combinations with inhibitors of the proteasome and of mTOR and also antihormones and steroidal metabolic enzyme inhibitors are especially useful because of their favourable profile of adverse effects.

In general, the combination of compound A with other cytostatic or cytotoxic agents makes it possible to pursue the following goals:
- improved efficacy in slowing the growth of a tumour, in reducing its size or even in completely eliminating it in comparison with treatment using an individual active ingredient;
- the possibility of employing the chemotherapeutics used in a lower dosage than in the case of monotherapy;
- the possibility of a more tolerable therapy with fewer adverse effects in comparison with individual administration;
- the possibility of treating a broader spectrum of tumour diseases;
- achieving a higher response rate to the therapy;
- longer patient survival time in comparison with current standard therapy.

Furthermore, compound A according to the invention can also be used in connection with radiotherapy and/or a surgical intervention.

EXAMPLES 1. Preparation of Compound A'

Compound A' was prepared according to the procedure described in example 2 of WO2014/076091.
2. In-vitro Experiments
2.1. Methods
2.1.1 Cell Lines

TABLE 1

List of the DLBLC cell lines investigated.

| Tumour indication | Subtype | Example cell line | Translocation (TL) or amplification (ampl) status |
|---|---|---|---|
| DLBCL | ABC[a] | HBL1 | MYC TL |
| DLBCL | ABC | OCI-LY-3 | MYC ampl/BCL2 ampl |
| DLBCL | ABC | TMD8 | MYC TL |
| DLBCL | GCB[b] | DB | BCL2 TL |
| DLBCL | GCB | SU-DHL-6 | MYC TL |
| DLBCL | GCB | HT | — |
| DLBCL | GCB | OCI-LY-19 | MYC TL |
| DLBCL | GCB | SU-DHL-8 | MYC TL/BCL2 TL |
| DLBCL | GCB | SU-DHL-10 | MYC TL/BCL2 TL |
| DLBCL | GCB | SU-DHL-4 | MYC ampl/BCL2 TL |
| DLBCL | GCB | SU-DHL-5 | — |

[a]activated B-cell type, [b]germinal-centre B-cell type 2.1.2 Cell Proliferation Assay The proliferation of all (DLCBL) cell lines in the presence of different concentrations of Compound A' or FR compound for 72 h was assessed using CellTiter Glo kits (Promega Corporation, Madison, Wis.). All expressed values were averages of triplicate experiments, and $IC_{50}$ was calculated using GraphPad Prism 5 (GraphPad Software, San Diego, Calif.) according to the manufacturer's instructions or the MTS software.

The FR compound is example 4 of WO2012/160034 and has a structure according to formula II:

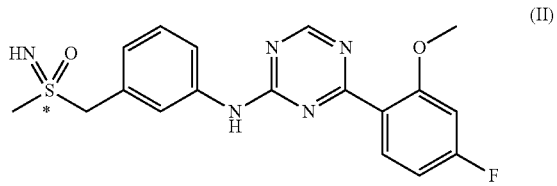 [SMILES: COc1cc(F)ccc1-c1ncnc(Nc2cccc(CS(C)(=N)=O)c2)n1]

2.2 In-Vitro Results

Table 2 summarizes the results in the proliferation assays with compound A' or FR compound.

TABLE 2

List of the cell lines investigated and results of the proliferation assay performed with compound A' or the FR compound.

| Tumour indication | Subtype | Example Cell line | Compound A' $IC_{50}$ [nmol/l] | FR compound $IC_{50}$ [nmol/l] |
|---|---|---|---|---|
| DLBCL | ABC | HBL1 | 196 | 540 |
| DLBCL | ABC | OCI-LY-3 | 83 | 340 |
| DLBCL | ABC | TMD8 | 100 | n/a |
| DLBCL | GCB | DB | 88 | 570 |
| DLBCL | GCB | SU-DHL-6 | 37 | 360 |
| DLBCL | GCB | HT | 81 | 710 |
| DLBCL | GCB | OCI-LY-19 | 39 | 480 |
| DLBCL | GCB | SU-DHL-8 | 93 | 610 |
| DLBCL | GCB | SU-DHL-10 | 129 | 600 |
| DLBCL | GCB | SU-DHL-4 | 90 | 170 |
| DLBCL | GCB | SU-DHL-5 | 105 | n/a |

These in vitro data indicate an efficient inhibition of the proliferation of both ABC (Activated B-cell type) and GCB (Germinal-centre B-cell type) subtypes of diffuse large B-cell lymphoma (DLBCL) by Compound A'. These data recommend Compound A' for the treatment of patients with DLBCL.

3. In-Vivo Experiment using OCL-LY-3 Diffuse Large B-Cell Lymphoma (DLBCL) Xenograft Model in Mice The aim of the present experiments was to assess the in vivo efficacy and tolerability of Compound A' in monotherapy in the DLBCL OCI-LY-3 tumour model subcutaneously implanted in SCID mice. In vivo efficacy was determined in female SCID mice bearing subcutaneous DLBCL OCI-LY-3 xenografts. Compound A' was assessed at one dose level in monotherapy. Anti-tumour activity and tolerability of the treated group was assessed using the vehicle control group as a reference.

For this purpose, OCI-LY-3 cells were subcutaneously injected (4×106 cells in 0.1 ml 100% Matrigel) in the right flank of female SCID mice (Charles River) Animals and tumour implants were monitored daily until the maximum number of implants showed clear signs of beginning solid tumour growth. At randomisation, the area of growing tumours was initially determined Animals bearing one tumour of an area of 25-35 mm2 were distributed in experimental groups according to the study protocol. The day of randomisation is designated as day 0 of an experiment Animals either received Compound A' (formulated in 30% PEG400/10% Ethanol/60%water), at a dose of 10 mg/kg q7d intravenously or vehicle control (qd po) for a period of 14 days.

Fatal toxicities did not occur and the maximum body weight loss was −6% in Compound A' group compared to −4% in the vehicle group indicating good tolerability of Compound A' at a dose of 10 mg/kg q7d iv.

At the end of the experiment Treatment to Control ratios (T/C) were calculated based on the mean tumor area and the mean tumor weight in the Compound A' treatment group and in the vehicle control group. The mean tumor weights and mean tumor areas were statistically significantly different, respectively. Compound A' reached a T/C by area of 0.29 and a T/C by weight of 0.24 demonstrating moderate in vivo activity of Compound A' in this model.

4. In-Vivo Experiment using SU-DHL-10 Diffuse Large B-Cell Lymphoma (DLBCL) Xenograft Model in Mice The aim of the present experiments was to assess the in vivo efficacy and tolerability of Compound A' in monotherapy in the DLBCL SU-DHL-10 tumour model subcutaneously implanted in SCID mice. In vivo efficacy was determined in female SCID mice bearing subcutaneous DLBCL SU-DHL-10 xenografts. Compound A' was assessed at one dose level in monotherapy. Anti-tumour activity and tolerability of the treated group was assessed using the vehicle control group as a reference. For this purpose, SU-DHL-10 cells were subcutaneously injected (10×106 cells in 0.2 ml 50% Matrigel) in the right flank of female SCID mice (Taconic M&B A/S, Denmark) Animals and tumour implants were monitored daily until the maximum number of implants showed clear signs of beginning solid tumour growth. At randomisation, the area of growing tumours was initially determined Animals bearing one tumour of an area of 25-35 mm2 were distributed in experimental groups according to the study protocol. The day of randomisation is designated as day 0 of an experiment Animals either received Compound A' (formulated in 30% PEG400/10% Ethanol/60%water), at a dose of 15 mg/kg q7d intravenously or vehicle control (q7d iv) for a period of 16 days.

The maximum body weight loss was −9% in Compound A' group compared to −4% in the vehicle group indicating moderate tolerability of Compound A' at a dose of 15 mg/kg q7d iv. At the end of the experiment the Treatment to Control ratios (T/C) was calculated based on the mean tumor area in the Compound A' treatment group and in the vehicle control group. The mean tumor areas were statistically significantly different. Compound A' reached a T/C by area of 0.02 demonstrating very high in vivo activity of Compound A' in this model corresponding to complete remissions.

4.5. SUMMARY AND CONCLUSION

These data indicate a significant and meaningful anti-tumour activity of Compound A' in patients with diffuse large B-cell lymphoma (DLBCL).

The invention claimed is:

1. A method of treatment and/or prophylaxis of diffuse large B-cell lymphoma, comprising administering an effective amount of 5-fluoro-4-(4-fluoro-2-methoxyphenyl)-N-{4-[(S-methylsulfonimidoyl)methyl]pyridin-2-yl}pyridin-2-amine of formula I or a physiologically acceptable salt or enantiomer thereof to a patient in need thereof

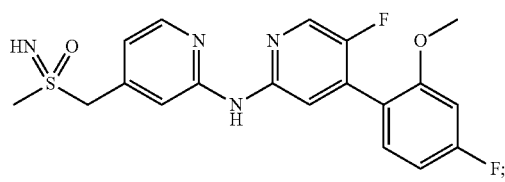

formula I wherein the diffuse large B-cell lymphoma is a diffuse large B-cell lymphoma which cells have an amplification or translocation of the MYC gene and/or BCL2 gene and/or an overexpression of the BCL2 protein.

2. The method according to claim 1, wherein the enantiomer (+)-5-Fluoro-4-(4-fluoro-2-methoxyphenyl)-N-{4-[(S-methylsulfonimidoyl)methyl]pyridin- 2-yl}pyridin-2-amine or a physiologically acceptable salt thereof is used.

3. The method according to claim 1, wherein the diffuse large B-cell lymphoma is a germinal-centre B-cell type of diffuse large B-cell lymphoma.

4. A method of treatment and/or prophylaxis of diffuse large B-cell lymphoma, comprising administering a pharmaceutical combination comprising an effective amount of 5-fluoro-4-(4-fluoro-2-methoxyphenyl)-N-{4-[(S-methylsulfonimidoyl)methyl]pyridin-2-yl}pyridin-2-amine of formula I or a physiologically acceptable salt or enantiomer thereof

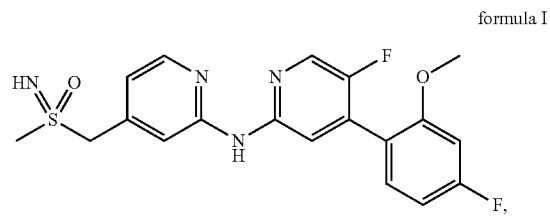 [SMILES: COc1cc(F)ccc1-c1cc(Nc2cc(CS(C)(=N)=O)ccn2)ncc1F]

formula I and at least one or more further active ingredients to a patient in need thereof;
wherein the diffuse large B-cell lymphoma is a diffuse large B-cell lymphoma which cells have an amplification or translocation of the MYC gene and/or BCL2 gene and/or an overexpression of the BCL2 protein.

5. The method according to claim 4, wherein the enantiomer (+)-5-Fluoro-4-(4-fluoro-2-methoxyphenyl)-N-{4-[(S-methylsulfonimidoyl)methyl]pyridin-2-yl}pyridin-2-amine or a physiologically acceptable salt thereof is used.

6. The method according to claim 4, wherein the diffuse large B-cell lymphoma is a germinal-centre B-cell type of diffuse large B-cell lymphoma.

7. A method of treatment and/or prophylaxis of diffuse large B-cell lymphoma, comprising administering a pharmaceutical composition comprising an effective amount of 5-fluoro-4-(4-fluoro-2-methoxyphenyl)-N-{4-[(S-methylsulfonimidoyl)methyl]pyridin-2-yl}pyridin-2-amine of formula I or a physiologically acceptable salt or enantiomer thereof

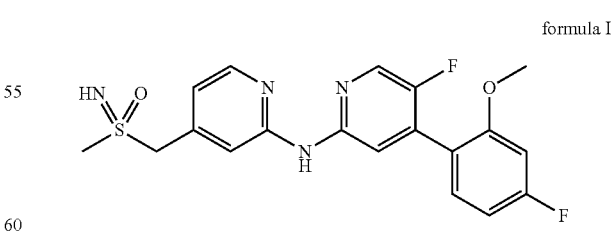

formula I and at least one inert, nontoxic, pharmaceutically suitable adjuvant to a patient in need thereof;
wherein the diffuse large B-cell lymphoma is a diffuse large B-cell lymphoma which cells have an amplification or translocation of the MYC gene and/or BCL2 gene and/or an overexpression of the BCL2 protein.

8. The method according to claim 7, wherein the enantiomer (+)-5-Fluoro-4-(4-fluoro-2-methoxyphenyl)-N-{4-[(S-methylsulfonimidoyl)methyl]pyridin-2-yl}pyridin-2-amine or a physiologically acceptable salt thereof is used.

9. The method according to claim 7, wherein the diffuse large B-cell lymphoma is a germinal-centre B-cell type of diffuse large B-cell lymphoma.

\* \* \* \* \*